(12) United States Patent
Savant

(10) Patent No.: US 9,811,640 B1
(45) Date of Patent: Nov. 7, 2017

(54) AUTOMATIC SELECTION OF TIME INTERVAL SIZE IN IMPLICIT TAU-LEAPING ALGORITHM

(75) Inventor: Shrikant Vitthal Savant, Shrewsbury, MA (US)

(73) Assignee: The MathWorks, Inc., Natick, MA (US)

( * ) Notice: Subject to any disclaimer, the term of this patent is extended or adjusted under 35 U.S.C. 154(b) by 2303 days.

(21) Appl. No.: 11/374,316

(22) Filed: Mar. 13, 2006

(51) Int. Cl.
*G06G 7/48* (2006.01)
*G06F 19/00* (2011.01)

(52) U.S. Cl.
CPC .................................. *G06F 19/70* (2013.01)

(58) Field of Classification Search
None
See application file for complete search history.

(56) References Cited

U.S. PATENT DOCUMENTS 7,769,576 B2    8/2010    Paxson et al.
2005/0187746 A1*   8/2005   Hicklin et al. .................. 703/11

OTHER PUBLICATIONS

Gillespie et al., J. Chem. Phys., Oct. 2003, vol. 119, No. 16, p. 8229-8234.*
Cao et al. , J. Chem. Phys., Aug. 2005, vol. 123, p. 1-8.*
Pastore et al., Circuits and Systems, Proceedings of the 1998 IEEE International Symposium, 1998, vol. 3, p. 452-455.*
Hassin et al., The Fibonacci Quarterly, 1981, vol. 19, p. 347-351.*
Gillespie et al. (J. Chem. Phys., Jul. 2001, vol. 115, No. 4, p. 1716-1733).*
J. Panyam, V. Labhasetwar, "Biodegradable nanoparticles for drug and gene delivery to cells and tissue", Advanced Drug Delivery Reviews, 55 (2003), pp. 329-347.
C. L. Liu, J. W. Layland, "Scheduling Algorithms for Multiprogramming in a Hard-Real-Time Environment", ACM 20, 1 (Jan. 1973), pp. 46-61.
D. T. Gillespie, "Exact Stochastic Simulation of Coupled Chemical Reactions", Journal of Physical Chemistry, vol. 81 (1977), pp. 2340-2361.
T. Rathinam, L. R. Petzold, D. T. Gillespie, "Stiffness in Stochastic Chemically Reacting System: The Implicit Tau-Leaping Method", Journal of Physical Chemistry, 15 vol. 119 (2003), 34 pages.
Swissprot database; http://us.expasy.org/sprot, retrieved online Nov. 11, 2013, 1 page.
National Center for Biotechnology Information: NCBI http://www.ncbi.nlm.nih.gov, retrieved online Nov. 11, 2013, 1 page.
Protein Data Bank http://www.rcsb.org/pdb, retrieved online Nov. 11, 2013, 2 pages.
Kyoto Encyclopedia of Genes and Genomics: KEGG http://www.genome.ad.jp/kegg/kegg2.html, retrieved online Nov. 11, 2013, 2 pages.

* cited by examiner

*Primary Examiner* — Pablo S Whaley
(74) *Attorney, Agent, or Firm* — Harrity & Harrity, LLP

(57) ABSTRACT

A modeling and simulation environment enables a user to create a model of a stiff chemical or biological system. The stiff chemical or biological system refers to a system that includes at least two or more different time scales of the chemical or biochemical reactions. The modeling and simulation environment also enables the user to solve the stiff chemical or biological system using a leaping algorithm. The leaping algorithm may leap over simulation of the reactions occurring in the time interval to accelerate the simulation of the chemical or biological system. The algorithm maximizes the size of the time interval by adjusting the size of the time interval using a bracketing algorithm.

34 Claims, 9 Drawing Sheets

Fig. 5

AUTOMATIC SELECTION OF TIME INTERVAL SIZE IN IMPLICIT TAU-LEAPING ALGORITHM

FIELD OF THE INVENTION

The present invention relates to simulation tools and, in particular, to tools for providing an improved environment for simulating chemical or biological systems.

BACKGROUND OF THE INVENTION

The development of new drug targets by the pharmaceutical industry is time-consuming and expensive because a large number of possible targets need to be tested before the molecule or compound with the desired properties is found or formulated. The same problem of a large number of possible variations affects the activities in the field of synthetic biology. In synthetic biology, biological entities are designed to perform a particular function, such as, for example, the development of biological nanomachines that may be used as programmed drug delivery systems. (See J. Panyam, V. Labhasetwar, Biodegradable nanoparticles for drug and gene delivery to cells and tissue, Advanced Drug Delivery Reviews, 55 (2003) 329-347.) As in drug discovery efforts, the formulation of a compound with desired properties is difficult due to the large variety of possible targets and the even larger context or system in which they must perform their function. Currently much of the work done to investigate the properties of these compounds is done in a wet-lab requiring many tedious and error prone experiments.

Development of chemical substances and nanomachinery, in addition to being time-consuming, can generate potentially dangerous intermediate substances. For example, a molecule used as a transport for a drug in a drug delivery system may, by its mere presence in the organism, stimulate the overproduction of some other protein. The overexpressed protein could act as a lethal toxin for the organism. Another possible complication is that the nanomachinery itself may mutate over time and either lose its original function or, worse, adversely interfere with the viability of the organism.

Another challenge facing the drug development activity is that, due to the cumbersome nature of experimental data collection, it is typical to limit experiments by narrowing the range of tested inputs and isolating the subsystem of interest. This limitation allows for the possibility that new drugs have unforeseen side-effects.

Moreover, current methods of obtaining data for biological processes are even more time-consuming than those associated with chemical processes, because the latter generally require laboratory experiments that lead to animal experiments and clinical trials. From these trials and experiments, data are obtained which, again, usually focus on a very narrow part of the biological system. Only after numerous costly trial-and-error clinical trials and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug. While conclusions may be drawn by assimilating experimental data and published information, it is difficult, if not impossible, to synthesize the relationships among all the available data and knowledge.

The various challenges faced by the aforementioned activities in chemical and biochemical research make it desirable to have software and methods for modeling, simulating, and analyzing biological processes in-silico rather than in-vitro or in-vivo. The goal of this approach is to provide a more comprehensive view of these biological systems prior to costly experiments and to clinical trials thereby reducing the search space for drug targets and useful nanoparticles.

Dynamic systems, such as biological processes and chemical reactions can be modeled as sets of differential, difference, algebraic, and/or recursive equations. At any given instant of time, these equations may be viewed as relationships between the system's output response ("outputs"), the system's input stimuli ("inputs") at that time, the current state of the system, the system parameters, and time. The state of the system may be thought of as a numerical representation of the dynamically changing configuration of the system. For instance, in a physical system modeling a simple pendulum, the state may be viewed as the current position and velocity of the pendulum. Similarly, a signal-processing system that filters a signal would maintain a set of previous inputs as the state. The system parameters are the numerical representation of the static (unchanging) configuration of the system and may be viewed as constant coefficients in the system's equations. For the pendulum example, a parameter is the length of pendulum and for the filter example; a parameter is the values of the filter taps.

Inherent in four of the classes of systems (ODE, difference equations, algebraic equations and composite) is the notion of system sample time. The sample-time is the time interval at which the inputs, state, or outputs (collectively referred to as the results) of the system are traced as time progresses. Based on sample times, a system can be described as a discrete-time system, continuous-time system and hybrid system. As noted above, stochastic systems occur at a random time determined by a reaction-specific operative probability distribution.

A discrete-time system is a system in which the evolution of the system results is tracked at finite intervals of time. In the limit as the interval approaches zero, the discrete-time system becomes a continuous-time system. The intervals of time may be periodic or non-periodic. Sometimes, non-periodic rate systems, such as stochastic systems, are referred to as non-uniform rate systems meaning that there is no periodic rate at which the response can be tracked. A continuous-time system is a system in which the evolutions of the system results are continuously changing. Continuous-time signals change during numerical integration. An example of a continuous-time system is one described by an ODE. There can also be algebraic or composite continuous-time systems. A hybrid system is a system with both discrete-time and continuous-time elements.

If a system has only one sample time, it is said to be single-rate. If a system has multiple sample times, it is said to be multi-rate. Multi-rate systems can be evaluated (executed) using either a single-tasking form of execution or a multi-tasking form of execution. When multi-tasking execution is used, it conforms to rate monotonic scheduling principals as defined by Liu, C. L., and LAYLAND, J. W. *Scheduling Algorithms for Multiprogramming in a Hard-Real-Time Environment.* ACM 20, 1 (January 1973), 46-61. Systems may also be categorized by the type of numerical integration solver being used. A fixed-step system is one that uses a fixed-step solver. Fixed-step solvers typically use explicit methods to compute the next continuous state at fixed periodic intervals of time. A variable-step system is one that is using a variable-step solver. A variable-step solver can use either implicit or explicit methods to compute the next continuous state at non-periodic intervals of time. Generally, variable-step solvers use a form of error control to adjust the interval size such that the desired error tolerances are achieved.

For biological process and chemical reaction models, stochastic solvers may be useful because stochastic reactions occur at a random time based on a reaction-specific probability distribution and hence they do not neatly fit either a fixed-step type of solver or a continuous-time solver. The stochastic solvers may use the exact stochastic simulation algorithm (SSA).

The exact SSA numerically simulates the time evolution of a given chemical system. In the SSA technique, reaction events given selected probabilities of occurring, and the events which occur change the probabilities of subsequent events. The algorithm determines, for a system in a given state, the next reaction to occur and the time that the next reaction occurs using probability. The algorithm is based on a quantity P(t, u), which is the probability that a reaction u will occur at the time interval t. The probabilities are based on the classical rate coefficients (k), the volume of the container, which can be a cell, a partition of a cell, a compartment of the cell, such as the nucleus or other organelles, or other container, and the concentration of reactants in a given reaction. Once a time and reaction have been computed, the method carries out the reaction, i.e., it updates the state of the system to reflect the transformation of reactants into products, then increments the time by t and determines another reaction to occur and when the reaction will occur. The SSA technique is described in detail in the article: Gillespie, D. T. 1977, *Exact Stochastic Simulation of Coupled Chemical Reactions*, Journal of Physical Chemistry, vol. 81, pp. 2340-2361.

Since the SSA simulates every reaction event, the simulation result of the SSA is accurate but it is too slow for practical simulation of the chemical or biological reaction systems. The tau-leaping algorithms have been proposed to accelerate the SSA by leaping over sequences of non-critical reactions that occur in a time interval, tau ($\tau$). In the tau-leaping algorithm, the size of the time interval is taken to encompass more than one reaction. Since the tau-leaping algorithms accelerate the SSA by sacrificing the accuracy of the simulation result, it is important to select the size of the time interval properly in order to balance the acceleration and accuracy of the simulation.

A recent article has proposed a method for determining the size of the time interval in an explicit tau-leaping algorithm, which is used to simulate non-stiff systems. See the article: D. T. Gillespie and L. R Petzold, *Improved Leap-Size Selection for Accelerated Stochastic Simulation*, Journal of Physical Chemistry, vol. 119 (2003), pp. 8229. The explicit tau-leaping algorithm, however, does not produce good results when applied to a stiff system. Therefore, an implicit tau-leaping algorithm has been proposed to address the stiffness of the system. See the article: T. Rathinam, L. R. Petzold, and D. T. Gillespie, *Stiffness in Stochastic Chemically Reacting System: The Implicit Tau-Leaping Method*, Journal of Physical Chemistry, vol. 119 (2003), pp. 11784-94. The article, however, does not provide a method for selecting the size of the time interval properly in the implicit tau-leaping algorithm. Automatic selection of the size of the time interval based on the model and the user input is necessary in a general purpose simulation tool.

SUMMARY OF THE INVENTION

The present invention provides a modeling and simulation environment for modeling and stochastically simulating a chemical or biological system having reactions with kinetics. The modeling and simulation environment enables a user to create a model of a stiff chemical or biological system. The stiff chemical or biological system refers to a system that includes at least two or more different time scales of the chemical or biochemical reactions. The modeling and simulation environment also enables the user to solve the stiff chemical or biological system using a leaping algorithm, such as an implicit tau-leaping algorithm. For example, the tau-leaping algorithm may leap over simulation of the reactions occurring in the time interval, tau ($\tau$), to accelerate the simulation of the chemical or biological system at the cost of user specified accuracy. The present invention maximizes the size of the time interval in the implicit leaping algorithm by adjusting the size of the time interval using a bracketing algorithm based on the user specified error tolerance. Determining the size of the time interval for stiff systems involves solving nonlinear algebraic equations in an iterative fashion because single step direct solutions are not possible.

According to an aspect of the present invention, a method is provided for simulating a system that comprises a plurality of chemical or biochemical reactions. The initial value of a time interval is determined for simulation of a stiff chemical or biological system using an explicit leaping algorithm. The stiff chemical or biological system includes at least two or more different time scales of the chemical or biochemical reactions. The initial value is adjusted using a bracketing algorithm to maximize the size of the time interval. The method leaps over the simulation of the stiff chemical or biological system during the time interval.

According to another aspect of the present invention, a computer-readable medium is provided for containing instructions executed to simulate a system that includes a plurality of chemical or biochemical reactions. The instructions are executed to determine the initial value of a time interval for the simulation of a stiff chemical or biological system using an explicit leaping algorithm. The stiff chemical or biological system includes at least two or more different time scales of the chemical or biochemical reactions. The instructions are also executed to adjust the initial value using a bracketing algorithm to maximize the size of the time interval. The simulation of the stiff chemical or biological system leaps over the time interval.

According to another aspect of the present invention, a tool is provided for simulation of a system that includes a plurality of chemical or biochemical reactions. The tool includes a modeling environment for accepting user commands and input to construct a model of a stiff chemical or biological system. The stiff chemical or biological system includes at least two or more different time scales of the chemical or biochemical reactions. The system also includes a simulation engine accepting as input the constructed model of the stiff biological system and generating as output dynamic behavior of the chemical or biological system using an implicit leaping algorithm. The simulation engine determines the initial value of a time interval and adjusts the initial value using a bracketing algorithm to maximize the size of the time interval. The simulation engine leaps over the time interval to accelerate the simulation of the stiff chemical or biological system.

BRIEF DESCRIPTION OF THE FIGURES

The invention is pointed out with particularity in the appended claims. The advantages of the invention described above, and further advantages of the invention, may be better understood by reference to the following description taken in conjunction with the accompanying drawings, in which:

FIG. 5 is another screenshot depicting an illustrative embodiment of a tabular modeling environment useful in connection with the present invention;

DETAILED DESCRIPTION OF THE INVENTION

Figure 1:
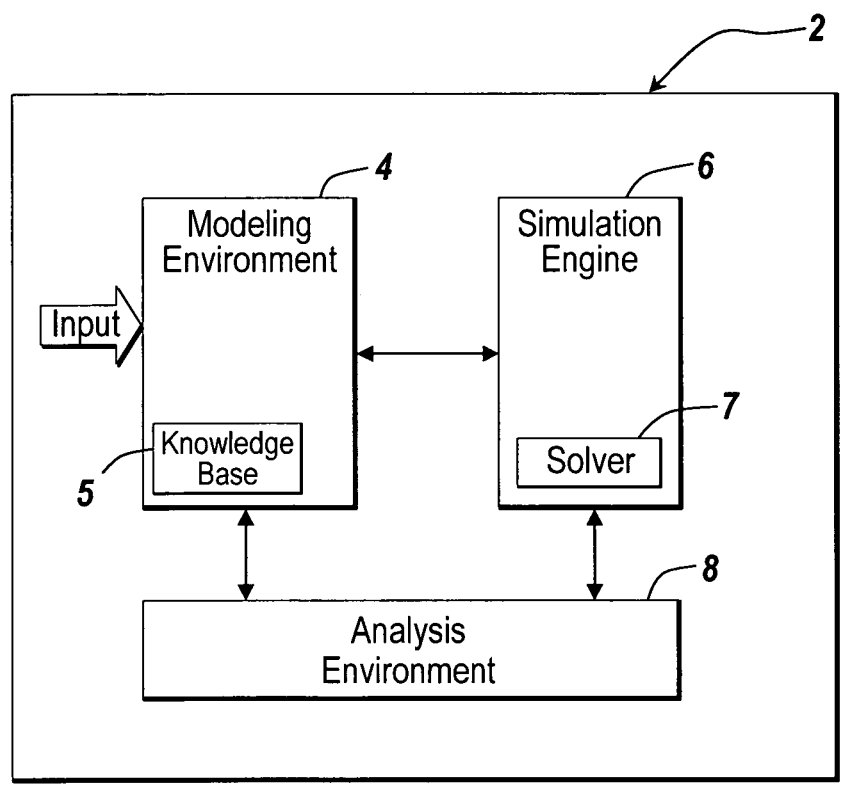
FIG. 1 is an exemplary modeling, simulation and analysis environment of the illustrative embodiment of the present invention.

Certain embodiments of the present invention are described below. It is, however, expressly noted that the present invention is not limited to these embodiments, but rather the intention is that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The illustrative embodiment of the present invention provides a simulation tool for simulating chemical or biological systems. The illustrative embodiment of the present invention provides a stochastic simulation tool for simulating the chemical or biological reactions in the chemical or biological systems.

SimBiology from The Mathworks, Inc. of Natick, Mass. is an exemplary simulation tool for the chemical or biological systems. SimBiology extends MATLAB with tools for modeling, designing, simulating, and analyzing biochemical pathways. A user can create his/her own model by manually entering in species, parameters, reactions, rules, kinetic laws, and units. The user can work with the kinetic laws and units built in to SimBiology or create his/her own. Both built-in and user-defined kinetic laws are stored in libraries for easy reuse and distribution. The user can also import Systems Biology Mark-Up Language (SBML) models. The user can simulate a model using stochastic or deterministic solvers, and graphically view the pathway in the block diagram explorer. The user can interact with SimBiology from the MATLAB command line or via a customizable graphical user interface (GUI). From the command line the user can execute all SimBiology functions and incorporate them into his/her own MATLAB applications. The GUI provides access to all command-line functionality and lets the user create and manage reactions, species, parameters, rules, units, and submodels.

Although the illustrative embodiment of the present invention is described relative to SimBiology, those of ordinary skill in the art will appreciate that SimBiology is an exemplary simulation tool and the present invention may apply to other chemical, biochemical or biological simulation tools.

In the illustrative embodiment, the simulation tool may include a modeling environment for constructing a model of a chemical or biochemical system that includes a number of chemical reactions. The tool may also include a simulation engine accepting as input the constructed model of the chemical or biochemical system and generating as output the dynamical behavior of the system as modeled. An analysis environment may communicate with the simulation engine and displays this result.

The illustrative embodiment provides a simulation tool for modeling, simulating and analyzing a stiff chemical or biochemical system. The stiff chemical or biochemical system refer to a system that includes at least two or more time scales of chemical or biochemical reactions in the system. In the stiff chemical or biochemical system, a current state of the system is evaluated as a function of the previous state of the system and the current state of the system. Hence it requires iterative solving as there are no single step direct solutions possible. In a non-stiff chemical or biochemical system, a current state of the system is evaluated as a function of the previous state of the system. Due to the nature of the equations, this solution can be obtained in a single step.

In the illustrative embodiment, the simulation engine may include solvers for simulating the dynamical behavior of the system. The solvers may include stochastic solvers, such as an explicit tau-leaping algorithm solver and an implicit tau-leaping algorithm solver. The explicit tau-leaping solver can be used for solving large, numerically non-stiff systems. The implicit tau-leaping solver is similar to the explicit tau-leaping solver but works optimally with numerically stiff systems. The implicit tau-leaping solver automatically chooses the time interval, tau, so that the relative change in the state of the system during the time interval is less than a user-defined error tolerance. The implicit tau-leaping solver maximizes the size of the time interval by adjusting the size of the time interval using a bracketing algorithm. When solving numerically stiff systems, the implicit tau-leaping solver remains stable at larger time intervals than the explicit tau-leaping solver.

FIG. 1 is a high-level block diagram of an exemplary simulation tool 2 for modeling, simulating, and analyzing chemical reactions and biological systems that include biological processes. The tool 2 may includes a modeling environment 4, a simulation engine 6, and an analysis environment 8. The simulation engine 6 communicates with the modeling environment 4. The simulation engine 6 receives models of chemical reactions or biological processes generated using the modeling environment 4. The simulation engine 6 communicates refinements to models created in the modeling environment 4. The analysis environment 8 is in communication with both the modeling environment 4 and the simulation engine 6. The analysis environment 8 may be used to perform various types of analyses directly on models created in the modeling environment 4. Also, the analysis environment 8 may receive and process results from the simulation engine 6 representing the execution by the simulation engine 6 of a model produced in the modeling environment. In other words, the simulation engine 6 generates the dynamic behavior of the model and communicates at least some of this dynamic behavior to the analysis environment 8. The analysis environment 8 may provide refinements to a model in the modeling environment 4 and may provide parameters for use by the simulation engine 6 when executing a model.

One of ordinary skill in the art will also appreciate that the modeling environment 4, simulation engine 6, and analysis environment 8 may be provided on the same computing device, which will be described below in more detail with reference to FIG. 2, or alternatively, the modeling environment 4, simulation engine 6, and analysis environment 8 may be coupled to each other via a communication network, which will be described below in more detail with reference to FIG. 3.

Figure 2:
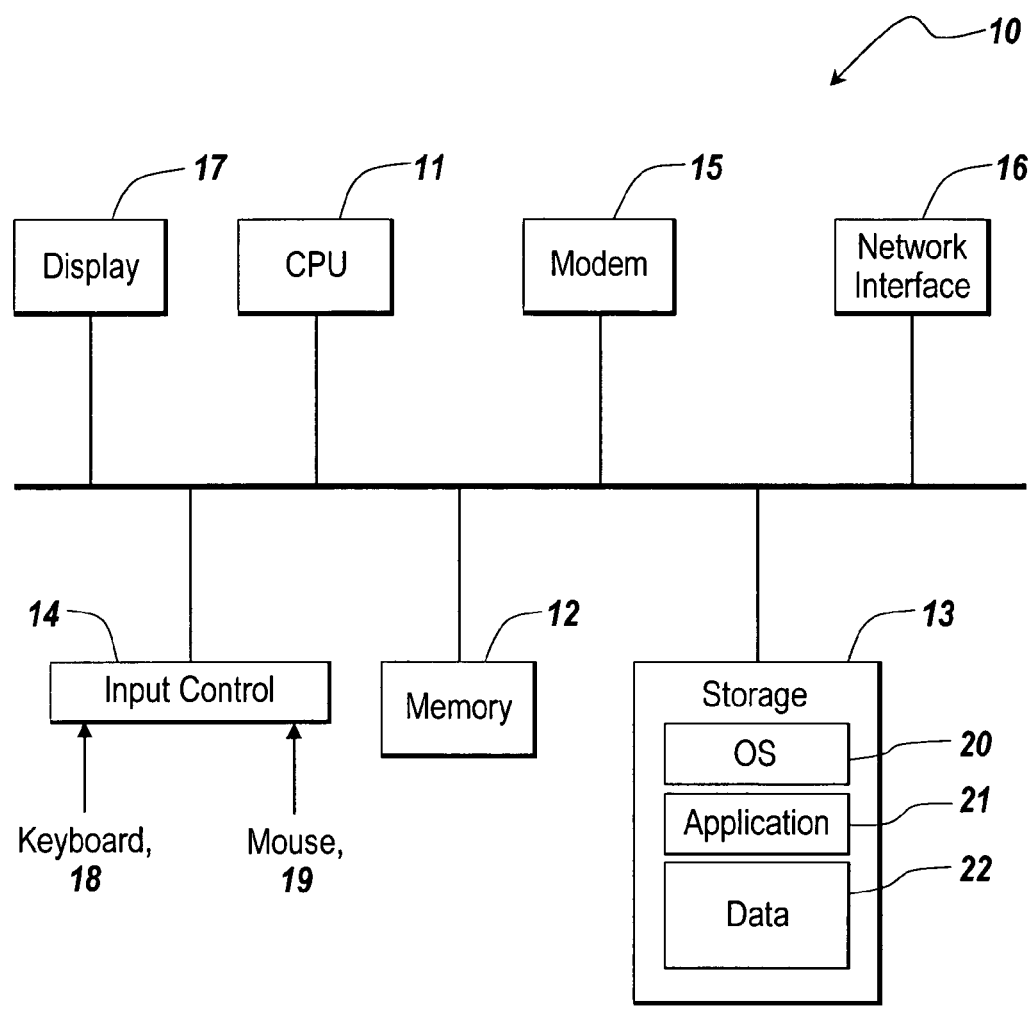
FIG. 2 is an exemplary block diagram of a computer system suitable for practicing the illustrative embodiment.

FIG. 2 is an exemplary computing device 10 suitable for practicing the illustrative embodiment of the present invention. One of ordinary skill in the art will appreciate that the computing device 10 is intended to be illustrative and not limiting of the present invention. The computing device 10 may take many forms, including but not limited to a workstation, server, network computer, quantum computer, optical computer, bio computer, Internet appliance, mobile device, a pager, a tablet computer, and the like.

The computing device 10 may be electronic and include a Central Processing Unit (CPU) 11, memory 12, storage 13, an input control 14, a modem 15, a network interface 16, a display 17, etc. The CPU 11 controls each component of the computing device 10 to provide the modeling environment 4, simulation engine 6, and analysis environment 8. The memory 12 temporarily stores instructions and data and provides them to the CPU 11 so that the CPU 11 operates the computing device 10 and runs the modeling environment 4, simulation engine 6, and analysis environment 8.

Optionally, the computing device 10 may include multiple CPUs for executing software loaded in the memory 12, and other programs for controlling system hardware. Each of the CPUs can be a single or multiple core processor. The code loaded in the memory 12 may run in a virtualized environment, such as in a Virtual Machine (VM). Multiple VM's may be resident on a single processor. Also, part of the application could be run in hardware, for example, by configuring a field programmable gate array (FPGA) or creating an application specific integrated circuit (ASIC).

The storage 13 usually contains software tools for applications. The storage 13 includes, in particular, code 20 for the operating system (OS) of the device 10, code 21 for applications running on the operation system including the applications for the modeling environment 4, simulation engine 6, and analysis environment 8, and data 22 generated from the modeling environment 4, simulation engine 6, and analysis environment 8. Those of ordinary skill in the art will appreciate that the application can be stored in the memory 12 as well, much like the data, and even the OS, or they can be stored on the network described below with reference to FIG. 3.

The input control 14 may interface with a keyboard 18, a mouse 19, and other input devices. The computing device 10 may receive through the input control 14 input data, such as the input data for determining the time interval, tau, which will be described below with reference to FIG. 8. The computing device 10 may display on the display 17 user interfaces 9 for displaying the data generated from the modeling environment 4, simulation engine 6, and analysis environment 8.

Figure 3:
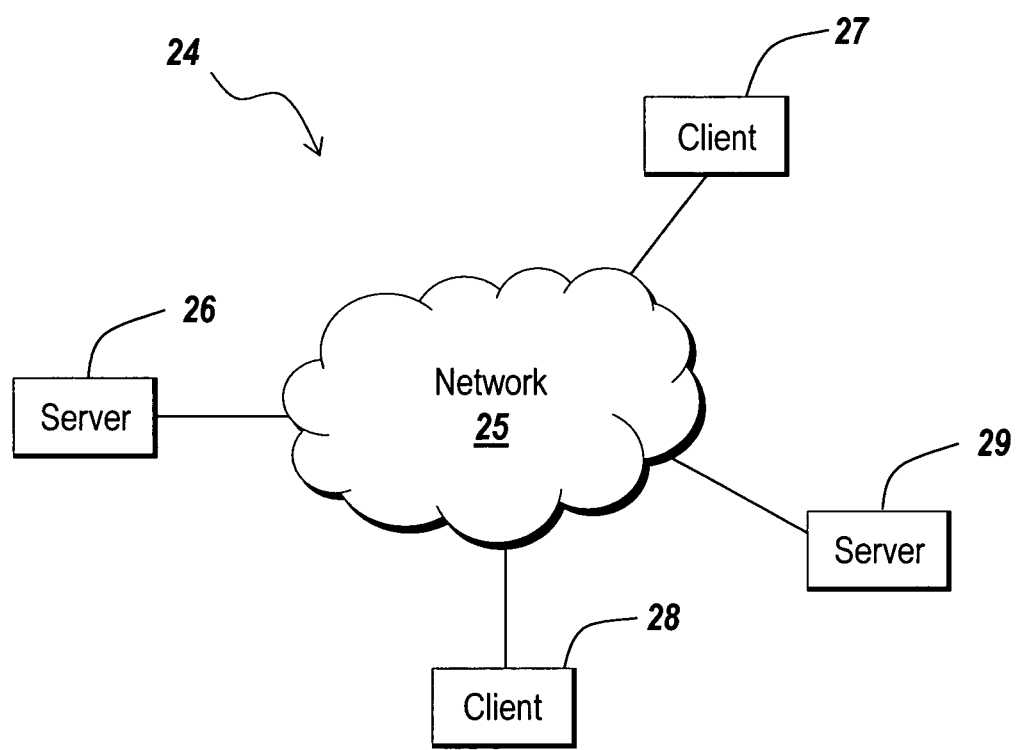
FIG. 3 is an exemplary network environment for the distributed implementation of the present invention.

FIG. 3 is an exemplary network environment 24 suitable for the distributed implementation of the illustrative embodiment. The network environment 24 may include one or more servers 26 and 27 coupled to clients 28 and 29 via a communication network 25. The network interface 16 and the modem 15 of the computing device 10 enable the servers 26 and 27 to communicate with the clients 28 and 29 through the communication network 25. The communication network 25 may include Internet, intranet, LAN (Local Area Network), WAN (Wide Area Network), MAN (Metropolitan Area Network), wireless network (e.g., using IEEE 802.11 and Bluetooth), etc. The communication facilities can support the distributed implementations of the present invention.

In the network environment 24, the servers 26 and 27 may provide the clients 28 and 29 with software components or products under a particular condition, such as a license agreement. The software components or products may include those for providing the modeling environment 4. The software components or products may also include those for the simulation engine 6, and analysis environment 8 coupled to the modeling environment 4. For example, the client 28 may perform the modeling of a chemical or biological system using a software component provided by the server 26 and send the server 26 the model for simulation or analysis. The server 26 then returns the simulation or analysis results to the client 28 and the client 28 may subsequently display the data to the user with the information on the data.

Referring back to FIG. 1, the modeling environment 4 accepts input to create a model of the chemical or biochemical reaction to be simulated. In some embodiments, the modeling environment 4 accepts input contained in a file, such as a file in Systems Biology Markup Language (SBML). In others of these embodiments, the file may be in HyperText Markup Language (HTML) format, Extensible Markup Language (XML) format, a proprietary markup language, or a text file in which fields are delimited by tabs or commas. Alternatively, the modeling environment 4 may accept input produced by a user via either a command-line interface or a graphical user interface.

The modeling environment 4 may include a plurality of reaction objects for defining each reaction in the chemical or biochemical system to be simulated. Each reaction object may encapsulate all of the information about a particular reaction that may be used when simulating the reaction.

Figure 4:
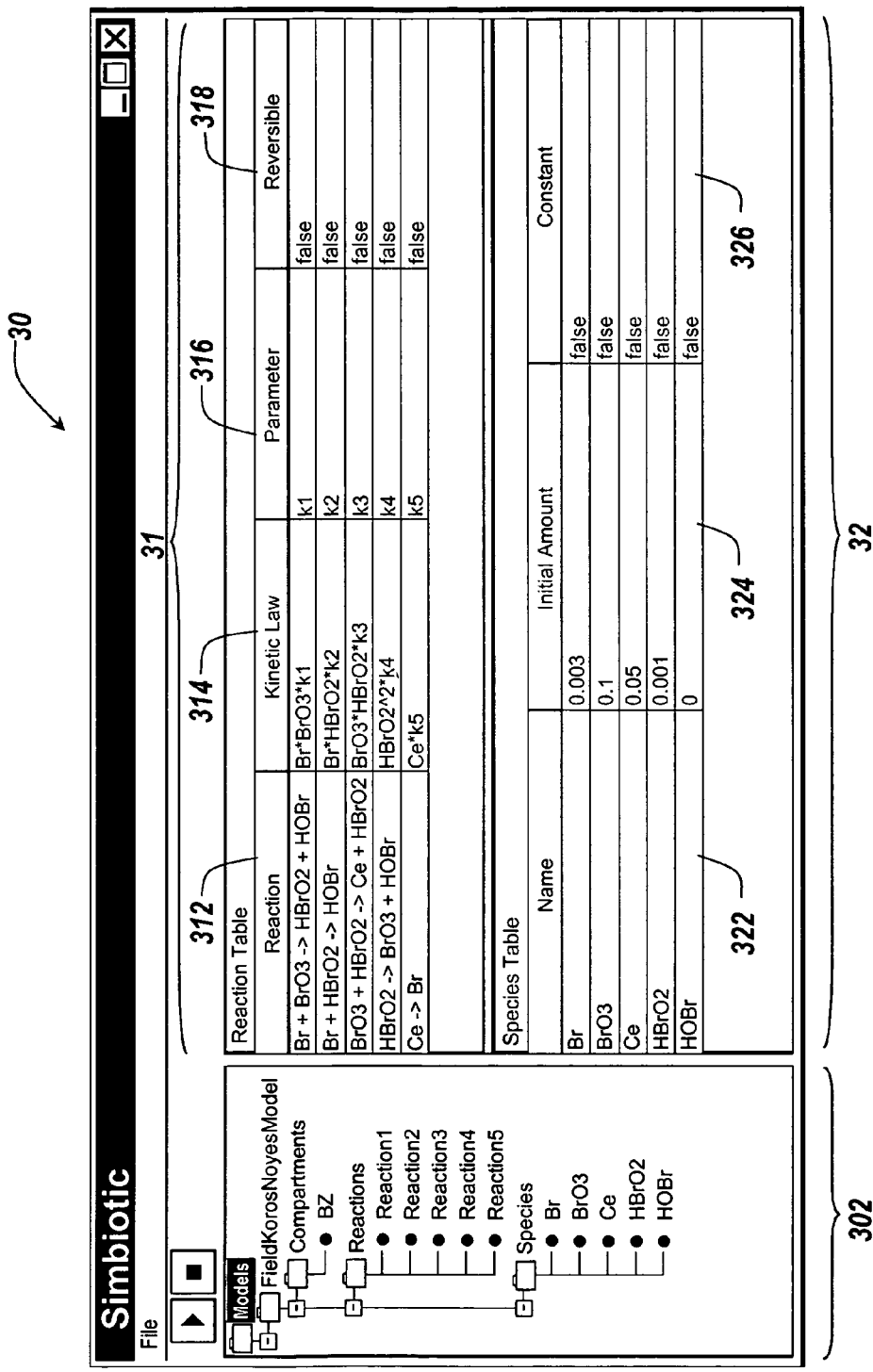
FIG. 4 is an exemplary screenshot depicting an illustrative embodiment of a tabular modeling environment useful in connection with the present invention.
Figure 5:
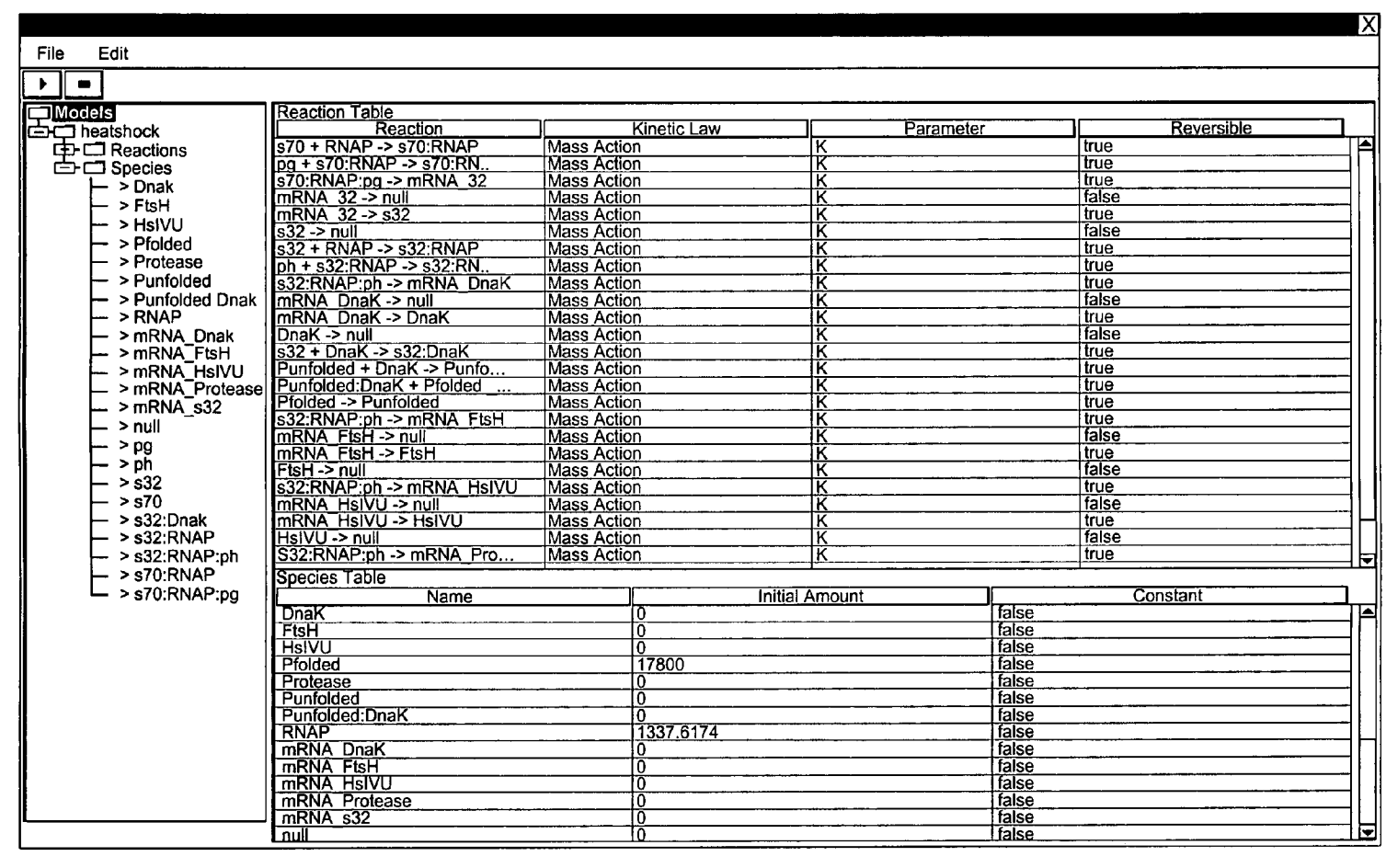

For example, a user can create a model of chemical or biochemical reactions using a graphical user interface, as shown in FIGS. 4 and 5. FIG. 4 depicts an embodiment of a tabular graphical user interface 30 that may be used to receive input manufactured by a user for creating a model. The user interface 30 may include a model pane 33. The model pane 33 may list one or more models in a tree structure familiar to users of computers operating under control of an operating system, such as the WINDOWS operating system manufactured by Microsoft Corp. of Redmond, Wash., or another suitable operating system using graphical controls. In the particular embodiment depicted by FIG. 4, a single model of a chemical reaction is contained in the model pane 33, indicated by the folder labeled "FieldKorosNoyesModel". That model contains three subfolders: "Compartments"; "Reactions"; and "Species". The subfolders represent pieces of the modeled reaction. Other graphical user interface schemes may be used to present this information to the user of the tool 2. In some embodiments, the model pane 33 may display a number of folders representing models. User selection of a particular folder causes the tool 2 to display folder in the model pane 33 that represent pieces of the reaction, e.g., compartments, reactions, and species. In still other embodiments, each model and all components of all models may be displayed in the model pane 33 and each model may be associated with a "radio button." Selection of the radio button associates with a model causes that model and its constituents to be actively displayed. In some of these embodiments, unselected models are displayed in grey type, or may have a transparent grey overlay indicating that they are not currently the active model.

The illustrative graphical user interface 30 may also include a reaction table 31, and a species table 32. The reaction table 31 is associated with the "Reactions" folder displayed in the model pane 33. Similarly, the species table 32 is associated with the "Species" folder displayed in the model pane 33. In some embodiments, collapsing the associated folder causes the table to not be displayed. The respective tables may be displayed in their own graphical user interface window, rather than in the same window as the graphical user interface 30.

The reaction table 31 lists each reaction present in a modeled biological process or chemical reaction. The modeling environment 30 displays reactions present in the Field-Koros-Noyes model of the Belousov-Zhabotinsky reaction and includes four columns: a reaction column 312, a kinetic law column 314, a parameter column 316, and a reversible column 318. Each row of the reaction table 31 corresponds to a particular reaction. The number and format of columns displayed by the reaction table may be selected by the user. In other embodiments, the modeling environment 4 may select the number and format of columns to display based on the type of reaction selected by the user.

The reaction column 312 may display a reaction represented in an abstract format, e.g., Ce→Br. In other embodiments, the reaction may be represented as a differential equation, in stochastic format, or as a hybrid of two or more of these formats. In some embodiments, the reaction table includes a column identifying modifiers of the reaction. For example, some reactions can be catalyzed by a substance. This may be represented in the tabular format as Ce–m(s)→Br, meaning that the presence of the species "s" accelerates the conversion of Ce into Br.

The reaction table 31 may also include a kinetic law column 314 which identifies the kinetic law expression the identified reaction follows. The kinetic law associated with the Ce→Br reaction is "Ce*k5," meaning that Ce is consumed at a rate controlled by the parameter "k5" and the amount of Ce present. The parameters for the kinetic law expression are listed in the parameter column 316. In some embodiments, the reaction table 31 includes a column identifying the name of the kinetic law associated with a particular reaction, e.g. "mass action" or "Michaels-Menten." In other embodiments, the reaction table 31 includes a column identifying the units in which the kinetic law parameters are expressed, e.g., 1/seconds, 1/(moles*seconds), etc.

The reaction table 31 may include a reversible column 318, which indicates whether the associated reaction is reversible. A reversible reaction is one which occurs in either direction, i.e. Ce<-> Br. In some embodiments the reaction table 31 may include a column identifying dynamics of the reaction, e.g., "fast" or "slow." In some of these embodiments, the rapidity with which a reaction occurs is identified on a scale of 1 to 10. In still other embodiments, the user may be presented with a slide control that allows the rapidity of various reactions to be set relative to one another. In still further embodiments, the reaction table 31 may include a column for annotations or notes relating to the reaction.

The interface 30 shown in FIG. 4 may also displays a species table 32. The species table 32 includes a name column 322, an initial amount column 324, and a constant column 326. The species table depicts the initial conditions and amounts of material used in the modeled biological process or chemical reaction. Thus, in the embodiment shown in FIG. 4, the modeled biological process begins with 0.003 molar units of bromine, i.e., 0.003 multiplied by Avrogado's number. The constant column 326 is set to "true" if the model should assume that there is an infinite supply of a particular species. In other embodiments the species table 32 includes other columns such as a column identifying units (e.g., moles, molecules, liters, etc.), whether a particular species is an independent variable in the model (i.e., whether the species is an input to the system), a column for annotations, or a column for notes. In some embodiments, the modeling environment 30 accepts as input a file in a markup language and converts that file into a graphical display of the sort depicted in FIG. 4. For example, a process may be provided that uses the information embedded in the tags of the markup language file, e.g., <reaction name="Reaction5" reversible="false">, to generate the tabular form of the model shown in FIGS. 4 and 5. In some of these embodiments, a web browser may be modified to parse files containing models written in markup language in order to create the tabular form of the model shown in FIGS. 4 and 5. In other embodiments, a process may accept the model as input and generate as output code that is directly executable on a processor, such a code written in the C programming language.

The model of a chemical or biochemical reaction created in the modeling environment may be converted into executable code. Conversion of a model into executable code allows the executable code to be transmitted to multiple computers via a network for execution on those computers. In these embodiments computers may be connected via a number of network topologies including bus, star, or ring topologies. The network can be a local area network (LAN), a metropolitan area network (MAN), or a wide area network (WAN) such as the Internet.

In these embodiments, a master server parses a model written in markup language. The model may be retrieved from a hard disk or from another computer accessed via a network connection. In other embodiments, the model is input by a user using a tabular user input such as the one shown in FIGS. 4 and 5 or a graphical user interface such as the one shown in FIG. 6. The master server parses the model to produce executable code. The executable code produced by the master server may be compiled code, such as code written in C, C+, C++, or C# and compiled to run on a target platform or the executable code produced by the master server may be a in a bytecode language such as JAVA. In some embodiments, the executable code is transmitted to one or more computers via a network connection. The one or more computers execute the code representing the model and return the generated result to the master server. The master server may store the retrieved results for later analysis. In some embodiments, the master server displays a graphical representation of each of the received results. In one embodiment, this technique is used to conduct Monte Carlo type analysis. In certain of these embodiments, the master server may collect and display each data point received and display each data point graphically in real-time.

FIG. 5 depicts in tabular form reactions for simulating the *E. Coli* heat shock response model according to an illustrative embodiment of the invention. As described above in connection with FIG. 4, the upper table displays the various reactions involved in transcription and translation of the heat shock proteins as well as the interactions of heat shock proteins with unfolded (or denatured) proteins. As depicted in FIG. 5, all reactions in the *E. Coli* heat shock response model have mass action kinetics and some are reversible, while some are not. Another method of representing chemical or biochemical reactions is by way of a block diagram.

Figure 6:
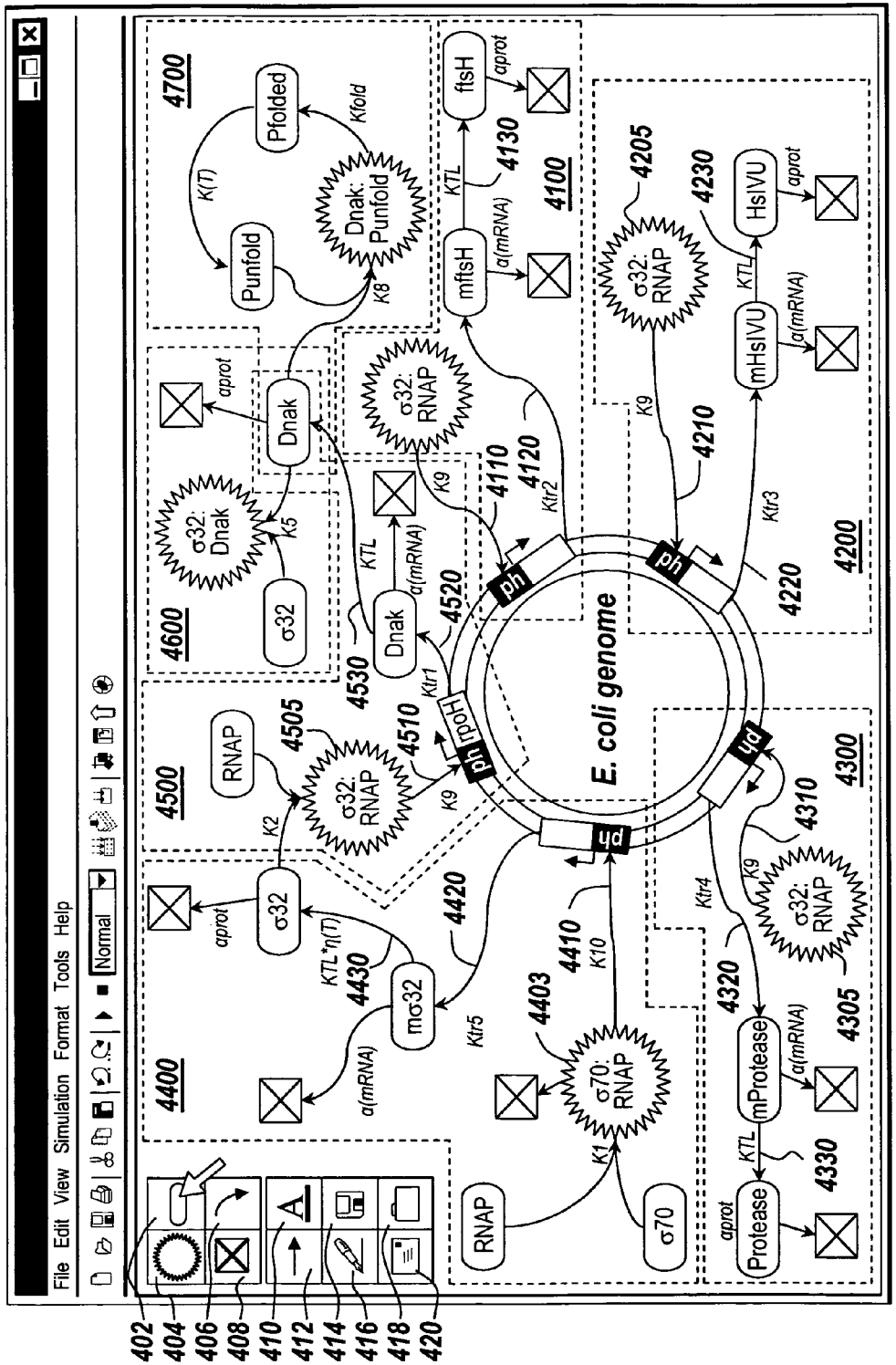
FIG. 6 is an exemplary graphical user interface that facilitates construction of block diagram representations of chemical reactions or biological processes.

In still other embodiments, the modeling environment 30 allows a user to represent a biological process or chemical reaction as a block diagram. FIG. 6 depicts an embodiment of a block diagram modeling environment. In the embodiment depicted in FIG. 6, a block diagram showing heat shock reaction in *E. Coli* bacteria is under construction. As is well known, heat shock response in *E. coli* is a protective cellular response to heat-induced stress. Elevated temperatures result in decreased *E. coli* growth, in large part, from protein unfolding or misfolding. The heat shock response, via heat shock proteins, responds to heat induced stress by refolding proteins via chaperones or by degrading nonfunctional proteins via proteases.

The block diagram shown in FIG. 6 depicts the expression of five particular gene sequences involved in the heat shock response. In part, FIG. 6 depicts pathways 4100, 4200, 4300 for the expression of proteases involved in heat shock response. Pathways 4100, 4200, 4300 represent the expression of heat shock proteins ftsH, Hs1VU and other proteases, respectively. The pathways 4100, 4200, 4300 are activated by the interaction 4105, 4205, 4305 of $\sigma^{32}$ with RNA polymerase at the promoter of the respective sequence. Each pathway 4100, 4200, 4300 depicts the transcription 4120, 4220, 4320 of the mRNA mediated 4110, 4210, 4310 by the $\sigma^{32}$ and RNA polymerase interaction 4105, 4205, 4305 at the promoter and the subsequent translation 4130, 4230, 4330 of the protease. The heat shock proteases, including ftsH and Hs1VU, serve to degrade proteins rendered nonfunctional by heat stress. Similarly, the diagram depicts the pathways 4400, 4500 involved in the expression of the heat shock proteins $\sigma^{70}$ and DnaK, respectively. The expression of the $\sigma^{32}$ protein is activated 4410 by the interaction 4403 of $\sigma^{70}$ and RNA polymerase at the promoter. The $\sigma^{32}$ mRNA is transcribed 4420 and, subsequently, $\sigma^{32}$ is translated 4430. In a closely related pathway 4500, the heat shock protein DnaK is translated. The interaction 4505 of $\sigma^{32}$ and RNA polymerase at the promoter activate 4510 the transcription 4520 of DnaK mRNA and, subsequently, the translation 4530 of DnaK. DnaK, in turn, may either interact 4600 with $\sigma^{32}$ so as to stabilize $\sigma^{32}$ or, alternatively, may refold 4700 the proteins unfolded by heat stress.

A block diagram editor, which is a component of the modeling environment, allows users to perform such actions as draw, edit, annotate, save, and print out block diagram representations of dynamic systems. Blocks are the fundamental mathematical elements of a classic block diagram model. In some of these embodiments, the modeling environment includes two classes of blocks, non-virtual blocks and virtual blocks. Non-virtual blocks are elementary dynamic systems, such as the $\sigma^{32}$ and RNA polymerase interaction 4105, 4205, 4305. A virtual block may be provided for graphical organizational convenience and plays no role in the definition of the system of equations described by the block diagram model. For example, in the block diagram of the heat shock mechanism in *E. Coli* bacteria depicted in FIG. 6, gene transcription mediated by σ32 to produce proteins, represented by 4100, 4200, and 4300, may be represented as a single, virtual block. In this case, the virtual block adds hierarchy to a model for the purpose of improving the readability of models.

The block diagram editor is generally a graphical user interface (GUI) component that allows drafting of block diagram models representing a chemical or biochemical reaction by a user. FIG. 6 depicts an embodiment of a GUI for a block diagram editor that features a floating element palette. In the embodiment shown in FIG. 6, the GUI tools include various block tools 402, 404, 408, various wiring line connection tools 406, 412, an annotation tool 416, formatting tool 410; a save/load tool 414, a notification tool 420 and a publishing tool 418. The block tools 402, 404, 408 represent a library of all the pre-defined blocks available to the user when building the block diagram. Individual users may be able to customize this palette to: (a) reorganize blocks in some custom format, (b) delete blocks they do not use, and (c) add custom blocks they have designed. The blocks may be dragged through some human-machine interface (such as a mouse or keyboard) on to the window (i.e., model canvas). The graphical version of the block that is rendered on the canvas is called the icon for the block. There may be different embodiments for the block palette including a tree-based browser view of all of the blocks. In these embodiments, the floating element palette allows a user to drag block diagram elements from a palette and drop it in place on the screen. In some of these embodiments, there may also be a textual interface with a set of commands that allow interaction with the graphical editor. For example, dragging a polymerase block to the model may cause the system to prompt the user for the protein to be used in the polymerase reaction.

Using this textual interface, users may write special scripts that perform automatic editing operations on the block diagram. A user generally interacts with a set of windows that act as canvases for the model. There can be more than one window for a model because models may be partitioned into multiple hierarchical levels through the use of subsystems. In still other embodiments, only a textual interface may be provided for facilitating the user's construction of the block diagram. The modeling environment 4 may also offer a variety of other GUI tools that improve the ability of users to build and manage large block diagrams. For example, wiring line connection tools 406, 412 allow users to draw directed lines that connect the blocks in the model's window. Connections may be added through various other mechanisms involving human-machine interfaces, such as the keyboard. The annotation tool 416 allows users to add notes and annotations to various parts of the block diagram. The formatting tool 410 enables users to perform various formatting operations that are generally available on any document editing tool. The save/load tool 414 allows a created block diagram model to be saved in a library or other suitable location for future use. A publishing tool 418 may be provided to enable the viewing of the block diagram as a document that can be published in any standard document formats (examples: PostScript, PDF, HTML, SBML, XML, SGML, SBML etc.). A notification tool 420 allows a user working on a block diagram to send a message to another user. In some embodiments, the notification tool 420 causes the current version of the block diagram, to be mailed to the specified user.

Those skilled in the art will also recognize that block-diagram packages offer scripting languages for writing out programs that automatically carry out a series of operations that would normally require interaction with the GUI, such as block addition, block deletion, starting and terminating execution, or modifying block attributes, etc.

The modeling environment 4 may also offer a variety of other GUI tools that improve the ability of users to build and manage large block diagrams. Examples of such GUIs include: (a) a Finder that helps find various objects such as blocks and lines within a block-diagram, (b) a Debugger that helps debug the execution of block-diagrams, (c) a Revision Control UI for managing multiple revisions of the block-diagram, and (d) a Profiler for viewing timing results while executing a block-diagram.

In some embodiments, the modeling environment 4 includes a knowledge base 5 that aids in construction of a model. In some of these embodiments, the knowledge base 5 contains models for various reactions, e.g. glycolysis. In these embodiments, when a user begins to input reactions consistent with a model for glycolysis, the knowledge base 5 may enter the remaining reactions for the user. Alternatively, the knowledge base 5 may offer different models of the reaction to the user. In some of these embodiments, the offered models represent the target reaction with varying levels of detail. In other embodiments, the knowledge base 5 may insert parameters or indications of reversibility for entered reactions. For example, the knowledge base 5 may specify a probability distribution that is suitable for the particular kinetics/dynamics of one or more entered reactions. The knowledge base 5 may also provide assistance to a user inputting a block diagram representation of a chemical or biochemical reaction. For example, the knowledge base 5 may prevent a user manufactured by connecting blocks inconsistent with the modeled reaction. Examples of publicly-available databases that may be used to facilitate generation of models include the Swiss Institute of Bioinformatics Swissprot database, the National Center for Biotechnology Information NCBI), the Research Collaboratory for Structural Bioinformatics (RCSB) Protein Data Bank, and The Kyoto Encyclopedia of Genes and Genomes (KEGG and KEGG2). Alternatively, the user may provide private databases to act as a knowledge base 5 for facilitating creation of models.

In other embodiments the knowledge base 5 may be used to facilitate further or broader understanding of the modeled reaction. For example, referring to the block diagram representation of the heat shock reaction in *E. Coli* bacteria, the knowledge base 5 can be used to identify other reactions in the heat shock reaction that use, or are impacted by, σ70. Alternatively, the knowledge base 5 may identify other reactions for *E. Coli* in which σ70 plays a part, e.g., chemotaxis. In this way, a broader understanding of the functioning of *E. Coli* in various environments can be achieved. In still other embodiments, the modeling environment 4 provides libraries from which blocks may be selected and included in a model. Models referenced by virtual or non-virtual blocks in a model, whether or not part of a library, are included in the model for execution. For embodiments in which executable code is generated, code representing the referenced models is also generated.

Once a block diagram model has been constructed within a modeling environment 4 using the tools described above, the chemical or biological reaction may be simulated by executing the model. An execution engine carries out the task of compiling and linking the block diagram to produce an "in-memory executable" version of the model that is used for generating code and/or simulating or linearizing a block diagram model. Execution of the block-diagram is also referred to as simulation. Model execution is carried out over a user-specified time span for a set of user-specified inputs. The execution begins when the block diagram is compiled. The compile stage marks the start of model execution and involves preparing data structures and evaluating parameters, configuring and propagating block characteristics, determining block connectivity, and performing block reduction and block insertion. The preparation of data structures and the evaluation of parameters create and initialize basic data-structures needed in the compile stage. For each of the blocks, a method forces the block to evaluate all of its parameters. This method is called for all blocks in the block diagram. If there are any unresolved parameters, execution errors are thrown at this point. During the configuration and propagation of block and port/signal characteristics, the compiled attributes (such as dimensions, data types, complexity, or sample time) of each block (and/or ports) are setup on the basis of the corresponding functional attributes and the attributes of blocks (and/or ports) that are connected to the given block through lines. The attribute setup is performed through a process during which block functional attributes "ripple through" the block diagram from one block to the next following signal connectivity. This process (referred to herein as "propagation"), serves two purposes. In the case of a block that has explicitly specified its block (or its ports') functional attributes, propagation helps ensure that the attributes of this block are compatible with the attributes of the blocks connected to it. If not, an error is issued. Secondly, in many cases blocks are implemented to be compatible with a wide range of attributes. Such blocks adapt their behavior in accordance with the attributes of the blocks connected to them. This is akin to the concept of polymorphism in object-oriented programming languages. The exact implementation of the block is chosen on the basis of the specific block diagram in which this block finds itself. Included within this step are other aspects such as validating that all rate-transitions within the model yield deterministic results and that the appropriate rate transition blocks are being used.

The compilation step also determines actual block connectivity. In this step, the virtual blocks in the block diagram, which play no semantic role in the execution of a block diagram, are optimized away (removed) and the remaining non-virtual blocks are reconnected to each other appropriately. This compiled version of the block diagram with actual block connections is used from this point forward in the execution process. The way in which blocks are interconnected in the block diagram does not necessarily define the order in which the equations (methods) corresponding to the individual blocks will be solved (executed). The actual order is partially determined during the sorting step in compilation. Once the compilation step has completed, the sorted order cannot be changed for the entire duration of the block diagram's execution.

Following the compilation stage is the model link stage. After linking has been performed, code may or may not be generated. If code is generated, the model is simulated/executed through accelerated simulation mode in which the block diagram model (or portions of it) is translated into either software modules or hardware descriptions (broadly termed code). If this stage is performed, then the stages that follow use the generated code during the execution of the block diagram. If code is not generated, the block diagram may execute in interpretive mode in which the compiled and linked version of the block diagram may be directly utilized to execute the model over the desired time-span. This interpretive mode of execution is suitable for getting fine-grained signal traceability. There are several different advantages to execution through code generation. Execution of generated code can be more efficient than interpretive execution because of fewer data-structures and lesser internal messaging in the engine, although the increased efficiency generally comes at the cost of decreased execution traceability. Simulation of hardware descriptions during execution can help identify and resolve bugs in the software stage of a design project. Such bugs prove much more expensive to track and fix once the system has been implemented in hardware. Additionally, block diagram modeling software can be integrated with other software environments that are suitable for modeling and simulating special classes of systems. Models can be tested directly in hardware thereby making prototyping of new systems fast and cost-effective. Those skilled in the art will recognize that when users generate code, they may choose to not proceed further with the block diagram's execution. They may choose to take the code and deploy it outside of the confines of the modeling software environment. This is normally the last step in the design of dynamic systems in a block diagram software package.

In one particular embodiment the modeling environment 4 provides a tool allowing a user to select the complexity with which a model executes. Referring back to FIG. 6 as an example, a user can be provided with a choice of executing pathway 4100 as a simple input-output block or executing pathway 4100 in the more detailed form shown in FIG. 6.

Figure 7:
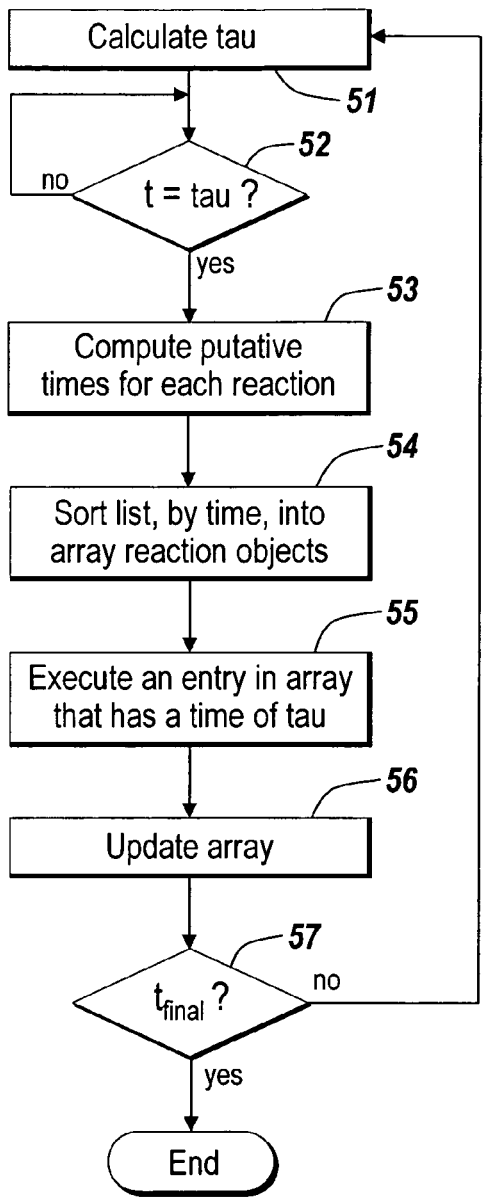
FIG. 7 is a flowchart of the exemplary steps taken to simulate a modeled biological process or chemical reaction using a stochastic solver.

Referring back to FIG. 1, the simulation engine 6 may include solvers 7 for solving the model created in the modeling environment 4. FIG. 7 illustrates the steps involved in simulating a biological or chemical system modeled using the implicit tau-leaping solver. In a first step, the solver calculates a time interval, tau ($\tau$), which will be described below in more detail with reference to FIGS. 9 and 10, and leaps over the simulation of the reactions in the time interval (steps 51 and 52). When the time reaches tau, the simulation determines putative times for each reaction in the model (step 53) using the probability distribution associated with each reaction, which is described in more detail in co-pending U.S. patent application Ser. No. 11/174,170 ("METHOD AND APPARATUS FOR INTEGRATED MODELING, SIMULATION AND ANALYSIS OF CHEMICAL AND BIOLOGICAL SYSTEMS HAVING A SEQUENCE OF REACTIONS, EACH SIMULATED AT A REACTION TIME DETERMINED BASED ON REACTION KINETICS") filed on Jun. 30, 2005, the content of which incorporated herewith by reference. During simulation, the simulation engine 6 retrieves the information for a particular reaction from a reaction object that includes information defining that reaction. Once putative reactions times are computed for each reaction in the system using a probability distribution particular to each reaction, the times are sorted, by putative occurrence time, into a state array (step 54). In one embodiment, the state array is an array of pointers sorted by occurrence time, each of the pointers pointing to the object to be executed at that point in model simulation. Once sorted, the simulation executes an object identified by the entry in the array that has the time of tau (step 55). Because execution of the object may affect the amount of species present in the modeled system or the putative reaction times for specific reactions in the table, the state array is updated to reflect the execution of the object (step 56). The simulation engine 6 checks to determine if the final simulation time has been reached (step 57). If not, the simulation engine 6 repeats the steps 51-57. Otherwise, the simulation terminates.

Figure 8:
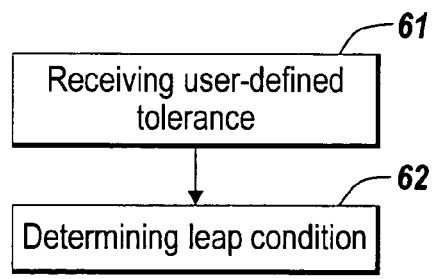
FIG. 8 is a flowchart of the exemplary steps taken to determine a leap condition in the illustrative embodiment.

FIG. 8 is a flowchart depicting one embodiment of the steps taken to determine a leap condition for calculating the time interval, tau. In the illustrative embodiment, the leap condition refers to a condition that enables the execution engine 6 to leap a time interval, tau. That is, the execution engine 6 can leap over a time interval as long as the leap condition is met in the time interval. In the illustrative embodiment, the leap condition is met if the relative change in the state of the system is less than a user specified tolerance over the time interval. The tool 2 may enable a user to input the tolerance for determining a leap condition (step 61). The user may input the data for the tolerance, such as 5% and 10%, using a graphical or text-based user interface. The tool 2 then determines the leap condition based on the user-defined tolerance that the relative change in the state of the system is less than a user specified tolerance over the time interval (step 62).

In the illustrative embodiment, the time interval, tau, is determined using a bracketing algorithm. The bracketing algorithm is used when it is known that the desired solution is sandwiched between two values, lower and upper limits of a bracket. In the implicit tau-leaping algorithm, the upper limit is characterized by the fact that the leap condition is always violated when the time interval is set equal to that value. Similarly, the lower limit is characterized by the fact that the leap condition is always satisfied at that value. Thus, the optimum value of the time interval is somewhere between the two limits. The illustrative embodiment maximizes the optimum value without violating the leap condition. The leap condition is satisfied if the actual error is within the acceptable error tolerance specified by the user.

Figure 9:
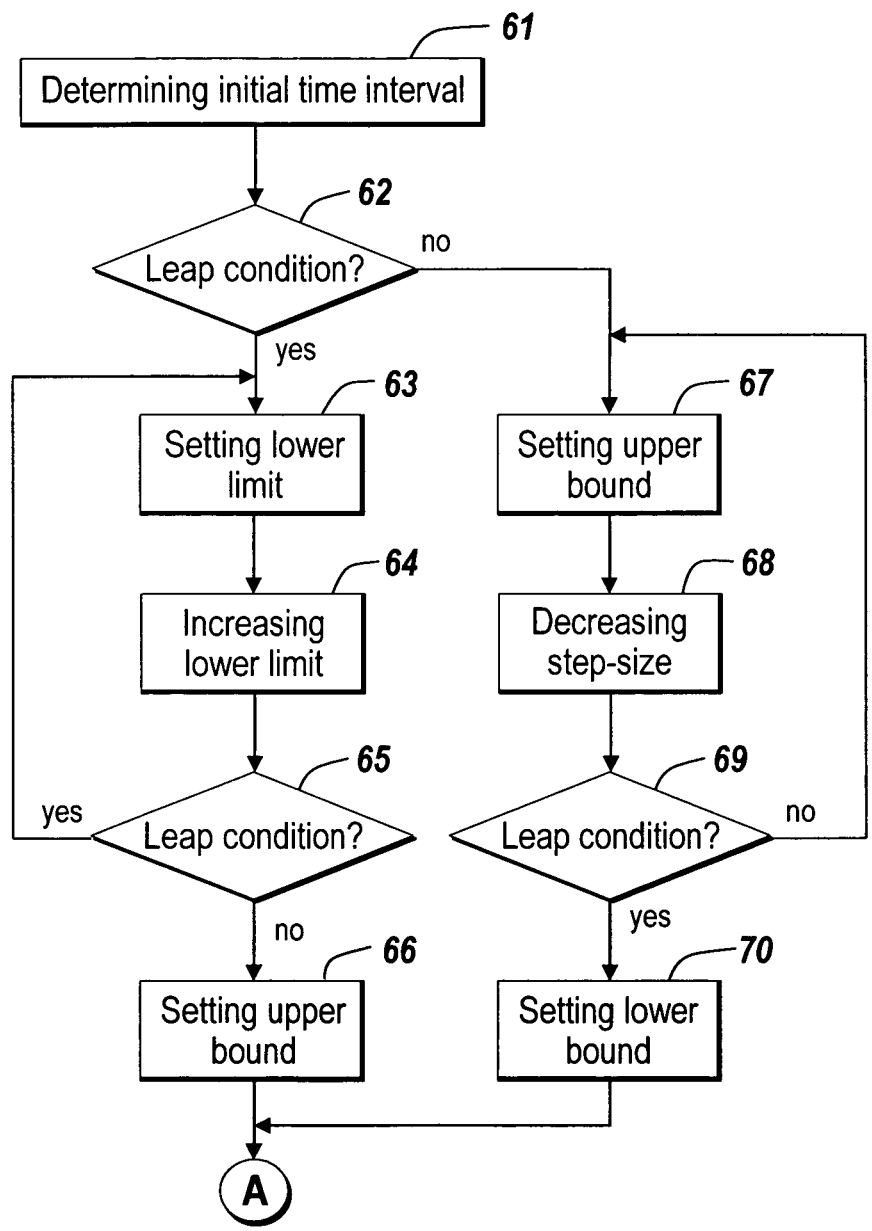
FIG. 9 is a flowchart of the exemplary steps taken to determine the lower and upper limits of a bracket in the illustrative embodiment.

FIG. 9 is a flowchart depicting one embodiment of the steps taken to determine the lower and upper limits of an initial bracket in the illustrative embodiment of the present invention. First, an initial value of the time interval is determined (step 61). In the illustrative embodiment, the initial value of the time interval is determined using an equation provided for determining a time interval in an explicit tau-leaping algorithm. Those of ordinary skill in the art will appreciate that the equation for determining a time interval in an explicit tau-leaping algorithm is illustrative and the initial value of the time interval can be determined using other methods, such as using a fixed value or a random value. After the time interval is initialized, it is determined whether the initial value of the time interval meets the leap condition (step 62). If the initial value of the time interval meets the leap condition, the value is set to the lower limit of a bracket (step 63). The value is then increased (step 64). In the illustrative embodiment, the value is increased using a golden section search ratio. Those of ordinary skill in the art will appreciate that the golden section search ratio is illustrative and the value can be increased using other methods or other ratios. After the value is increased, it is determined whether the leap condition is met with the increased value (step 65). If the increased value meets the leap condition, steps 63 and 64 are repeated using the increased value. If the increased value does not meet the leap condition, the increased value is set to the upper limit of the bracket (step 66).

In step 62, if the initial value of the time interval does not meet the leap condition, the value is set to the upper limit of a bracket (step 67). The value is then decreased (step 68). In the illustrative embodiment, the value is decreased using a golden section search ratio. Those of ordinary skill in the art will appreciate that the golden section search ratio is illustrative and the value can be decreased using other methods or other ratios. After the value is decreased, it is determined whether the leap condition is met with the decreased value (step 69). If the decreased value does not meet the leap condition, steps 67 and 68 are repeated using the decreased value. If the decreased value meets the leap condition, the decreased value is set to the lower limit of the bracket (step 63).

Figure 10:
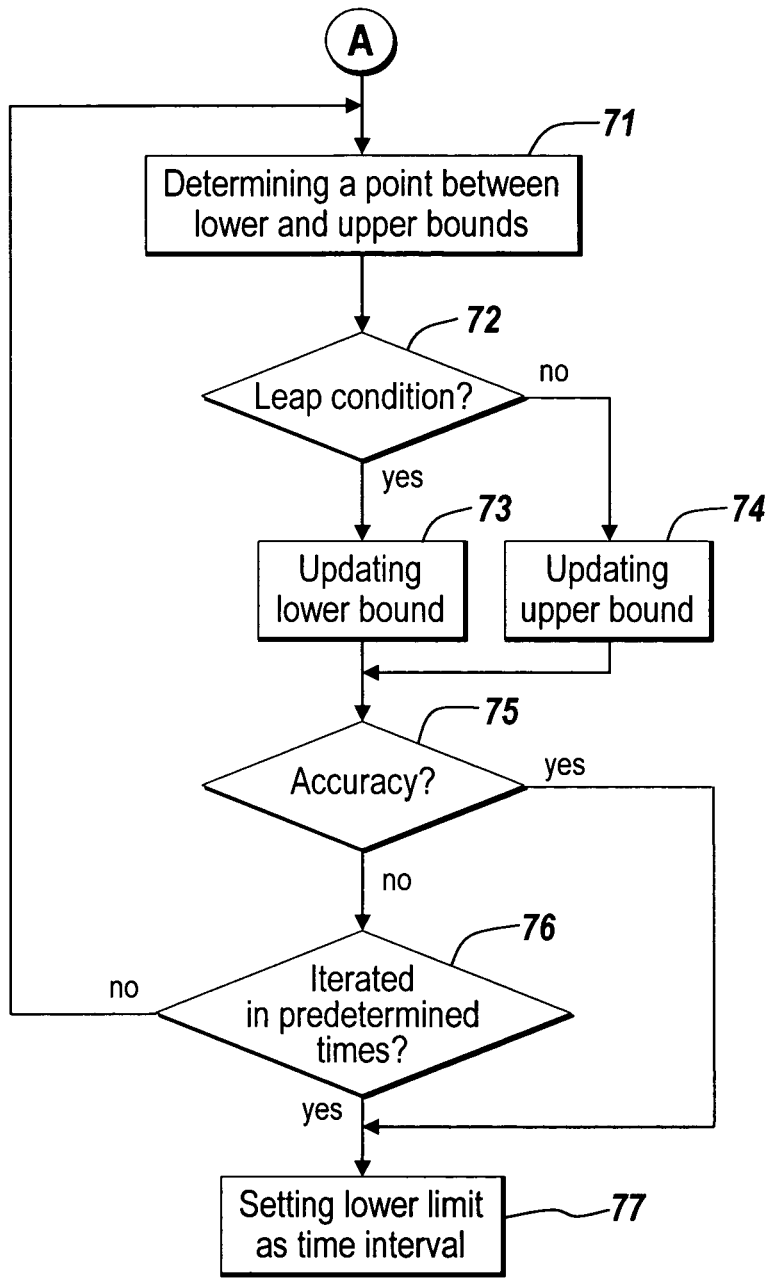
FIG. 10 is a flowchart of the exemplary steps taken to determine the size of the time interval in the illustrative embodiment.

FIG. 10 is a flowchart depicting one embodiment of the steps taken to determine the optimal value of the time interval within the bracket. A point is determined between the lower and upper limits of the bracket (step 71). In the illustrative embodiment, the point is determined using a golden section search ratio. Those of ordinary skill in the art will appreciate that the golden section search ratio is illustrative and the point can be determined using other methods or other ratios. After the point is determined, it is determined whether the leap condition is met with the point (step 72). If the point meets the leap condition, the lower limit of the bracket is updated with the point (step 73). If the point does not meet the leap condition, the upper limit of the bracket is updated with the point (step 74). It is then determined whether the distance between the lower and upper limits of the bracket is less than a predetermined value (step 75). The predetermined distance is set to ensure that the calculation of the time interval is accurate. The predetermined distance can be specified by a user. The predetermined distance is used to determine whether the calculated time interval is optimal and accurate. If the distance between the lower and upper limits of the bracket is less than a predetermined value, the lower limit of the bracket is set to the optimal value of the time interval, tau (step 77). If the distance between the lower and upper limits of the bracket is not less than a predetermined value, steps 71-75 are iterated for predetermined times (step 76). After steps 71-75 are iterated for predetermined times, the lower limit of the bracket is set to the optimal value of the time interval, tau (step 77).

Referring back to FIG. 1, the results generated by the simulation engine 6 may be used by an analysis environment 8. In other embodiments, the analysis environment 8 operates directly on a model, for example, to generate a steady-state value for a modeled system instead of simulating the system. In some of these embodiments, the analysis environment 8 does this by setting the derivative of all differential equations to 0 and solving the system algebraically. In others of these embodiments, the analysis engine performs a flux-balance analysis, as is known in the art, to determine the steady-state value of a system. Other well-known forms of analysis that may be employed by the analysis environment 8 include using non-linear solvers, sensitivity analysis, bifurcation analysis, parameter scans, parameter estimation and network inference analysis. The result of these analyses may be provided to the simulation engine 6 as input for its calculations.

The analysis environment 8 may further process the results generated by the simulation engine 6 or it may display the results visually or auditorially. For example, the analysis environment 8 may use graph visualization techniques to identify to a user similar pathways. In some embodiments the analysis environment 8 interfaces with data acquisition hardware (not shown in FIG. 1) which allows the analysis environment 8 to compare the generated results with experimental data. In these embodiments, data gathered from an ongoing experiment is used to correct or generate a model of the reaction that is occurring in situ. In some embodiments the experiment is conducted on a microarray or a gene chip. For example, if the existence of a given protein is predicted by a model but data acquired from the experiment indicates that the protein does not exist, the analysis environment 8 may signal a user, either auditorially or visually, that the in situ experiment and the predicted response differ. For embodiments in which the experiment is conducted on a microarray, the gathered data may differ between microwells. In these embodiments, the analysis environment may average the value of the gathered data. In others of these embodiments, the analysis environment 8 may signal a difference if the data from a single microwell differs from the model's predicted response. In some embodiments, the amount of tolerable difference between the in situ experiment and the predicted result is user-configurable. In other embodiments, the analysis environment transmits the gathered data to the modeling environment 4 so that the model may be modified to account for the difference. In still other embodiments, the analysis environment 8 graphically displays the expected result of the experiment and data gathered from the experiment.

In other embodiments, the data acquisition hardware allows the analysis environment to control an experiment that is in progress based on the results generated by the simulation engine 6. These embodiments may be useful in construction of nanomachinery. In these embodiments, a model may call for in situ temperature to be at 102 degrees Fahrenheit. If a thermocouple measuring temperature of the in situ environment indicates that the temperature has fallen below 102 degrees Fahrenheit, more heat may be applied to the experiment.

Data acquisition hardware may include any of a number of hardware devices compatible with the computing platform executing the integrated modeling, simulation, and analysis environment. For example, in embodiments in which the environment 100 executes on a personal computer, the data acquisition hardware interfaces with the local system bus. In embodiments such as those shown in FIG. 5, the data acquisition hardware interfaces with the Hyper-Transport bus, Rapid I/O bus, or InfiniBand. The data acquisition hardware can communicate with instruments and experiments that use GPIB (IEEE-488, HPIB), VISA, TCP/IP, and UDP standards.

Although the systems and methods of the present invention have been described above as executing on a single machine, they may also be used in a client-server environment such as X-Windows or Microsoft Terminal Services, as described above with reference to FIG. 3. The modeling environment 4, simulation engine 6, and analysis environment 8 may each execute on separate machines, or they may be aggregated in any combination between machines. For example, in one particular embodiment, the modeling environment 4 and the analysis environment 8 execute on a "client" machine while the simulation engine executes on a "server" machine. In these embodiments, the computers may be connected via a number of network topologies including bus, star, or ring topologies. The network can be a local area network (LAN), a metropolitan area network (MAN), or a wide area network (WAN) such as the Internet. The respective computers may connect to the network 180 through a variety of connections including standard telephone lines, LAN or WAN links (e.g., T1, T3, 56 kb, X.25), broadband connections (ISDN, Frame Relay, ATM), and wireless connections. Connections can be established using a variety of communication protocols (e.g., TCP/IP, IPX, SPX, NetBIOS, NetBEUI, SMB, Ethernet, ARCNET, Fiber Distributed Data Interface (FDDI), RS232, IEEE 802.11, IEEE 802.11a, IEE 802.11b, IEEE 802.11g and direct asynchronous connections). An embodiment of the present invention relates to a computer storage product including a computer-readable medium having computer code thereon for performing various computer-implemented operations. The media and computer code may be those specially designed and constructed for the purposes of the present invention, or they maybe of the kind well known and available to those having skill in the computer software arts. Examples of computer-readable media include, but are not limited to: magnetic media such as hard disks, floppy disks, and magnetic tape; optical media such as CD-ROMs, CD-R/RW discs, DVD-ROMs, DVD-RAMs, and holographic devices; magneto-optical media such as floptical disks; solid-state memories such as flash drives, memory sticks, xD cards, MultiMedia cards, and Smart Media cards; and hardware devices that are specially configured to store and execute program code, such as application-specific integrated circuits ("ASICs"), field-programmable gate arrays (FPGAs), programmable logic devices ("PLDs"), read only memories ("ROMs"), random access memories ("RAMs"), erasable programmable read only memories ("EPROMs"), and electrically erasable programmable read only memories ("EEPROMs").

Examples of computer code that may be embodied on such computer-readable media include machine code, such as produced by a compiler, and files containing higher level code that are executed by a computer using an interpreter. For example, an embodiment of the invention may be implemented using Java, C++, or other object-oriented programming language and development tools.

Although the illustrative embodiment of the present invention is described above with reference to chemical or biological systems, the present invention can be extended to discrete event systems that are characterized by discrete events activated by specific conditions or trigger conditions. A bio-chemical reaction network wherein a specific reaction is triggered when the concentration of a particular species reaches a certain value is an example of a discrete event system. The reaction gets triggered not based on time, but based on some other event happening, which may be the concentration of the particular species reaching a certain value. Another example of the discrete event systems may be the stock market. The stock market goes up or down based on some event like the interest rate hike announced by the Federal Reserve Board. The actual trigger conditions may vary depending on the system and the application. The simulation of a discrete event system is characterized by a response to various discrete events. This is unlike a deterministic system in which simulation progresses based on time.

Events in a discrete event system have some propensity function associated with them and the event is triggered depending upon the value of the associated propensity function. The propensity function determines the probability of that event happening. The simulation then progresses depending upon which events are triggered and in what order. During simulation of such a system, one has to select the time-step carefully. If very large steps are taken, important events in between may be skipped. If very small steps are taken, no useful events may be triggered in the time intervals and the total simulation may take a very long time.

The algorithm described above can be used to select the time-step while simulating a discrete event system. The details of the "Leap Condition", which indicate whether the given time step is acceptable or not, may vary depending upon the application and is defined by the user. For simulation of a bio-chemical reaction network, the "Leap Condition" may mean that the relative change in the propensity function must be less than a user-specified tolerance. For other discrete event systems, it may mean something different.

Therefore, it should be understood by those skilled in the art that various changes may be made and equivalents substituted without departing manufactured by the spirit and scope of the invention defined by the appended claims. In addition, modifications may be made to adapt to a particular situation, material, composition of matter, method, process, series of steps to the objective of the present invention while staying within the spirit and scope of the invention and such modifications are intended to be within the scope of the appended claims. In particular, while the methods disclosed have been described with reference to particular steps in a particular order, it will be understood that these steps may be combined, sub-divided, or reordered to form an equivalent method without departing manufactured by the teachings of the present invention. Accordingly, unless specifically indicated herein, the order and grouping of steps is not a limitation of the present invention.

The invention claimed is:

1. A method comprising:
   determining an initial value of a time interval for execution of a model using a leaping algorithm,
      the model being associated with a chemical system or a biological system, and
      the determining being performed by a computing device;
   adjusting the initial value of the time interval using a bracketing algorithm,
      the adjusting being performed by the computing device, and
      the adjusting comprising:
         providing an upper limit for the time interval and a lower limit for the time interval; and
         determining, a first time, if a leap condition is satisfied for the model over the time interval,
            the determining if the leap condition is satisfied comprising:
               setting the lower limit for the time interval as the initial value and increasing the initial value when the leap condition is satisfied, and
               setting the upper limit for the time interval as the initial value and decreasing the initial value when the leap condition is not satisfied;
      comparing a distance between the lower limit and the upper limit to a predetermined distance,
         the lower limit being selected as a final time interval when the distance between the lower limit and the upper limit is less than the predetermined distance,
         the determination if the leap condition is satisfied being performed a second time when the distance between the lower limit and the upper limit is greater than the predetermined distance, and
         the comparing being performed by the computing device;
   simulating the chemical system or the biological system using the model and using time steps corresponding to the final time interval to generate a simulation result,
      the simulating being performed by the computing device; and
   outputting the simulation result for analysis,
      the outputting being performed by the computing device.

2. The method of claim 1, where the leaping algorithm comprises a tau($\tau$)-leaping algorithm.

3. The method of claim 2, where a state of the model at time (t+τ) is a function of a state of the model at time t and the state of the model at time (t+τ).

4. The method of claim 2, where the initial value of the time interval is determined by an equation provided for a non-discrete τ-leaping algorithm.

5. The method of claim 2, where a state of the model at time (t+τ) is provided as a function of a state of the model at time t.

6. The method of claim 1, further comprising:
determining the leap condition based on a user-defined tolerance of a relative change in a state of the model.

7. The method of claim 1, where the lower limit satisfies the leap condition and the upper limit does not satisfy the leap condition.

8. The method of claim 1, where the initial value of the time interval is increased or decreased using a predetermined ratio.

9. The method of claim 1, further comprising:
determining a point between the lower limit and the upper limit; and
determining whether the point satisfies the leap condition.

10. The method of claim 9, further comprising:
updating, a first time, the lower limit with the point when the point satisfies the leap condition; or
updating, a first time, the upper limit with the point when the point does not satisfy the leap condition.

11. The method of claim 10, further comprising:
updating the lower limit a second time;
updating the upper limit a second time; and
setting, based on updating the lower limit the second time and updating the upper limit the second time, a size of the time interval to the lower limit.

12. The method of claim 1, where a plurality of discrete events, associated with the model, are associated with at least two different time scales.

13. A non-transitory computer-readable medium storing instructions, the instructions comprising:
one or more instructions which, when executed by at least one processor, cause the at least one processor to:
determine an initial value of a time interval for execution of a model using a leaping algorithm,
the model being associated with a chemical system or a biological system;
adjust the initial value of the time interval using a bracketing algorithm, the one or more instructions to adjust the initial value including:
one or more instructions to provide an upper limit for the time interval and a lower limit for the time interval; and
one or more instructions to determine, a first time, if a leap condition is satisfied for the model over the time interval, the one or more instructions to determine if the leap condition is satisfied including:
one or more instructions to set the lower limit for the time interval as the initial value and increase the initial value when the leap condition is satisfied, and
one or more instructions to set the upper limit for the time interval as the initial value and decrease the initial value when the leap condition is not satisfied;
compare a distance between the lower limit and the upper limit to a predetermined distance,
the lower limit being selected as a final time interval when the distance between the lower limit and the upper limit is less than the predetermined distance, and
the determination if the leap condition is satisfied being performed a second time when the distance between the lower limit and the upper limit is greater than the predetermined distance;
simulate the chemical system or the biological system using the model and using time steps corresponding to the final time interval to generate a simulation result; and
output the simulation result for analysis.

14. The non-transitory computer-readable medium of claim 13, where the leaping algorithm comprises a tau(τ)-leaping algorithm.

15. The non-transitory computer-readable medium of claim 14, where a state of the model at time (t+τ) is a function of a state of the model at time t and the state of the model at time (t+τ).

16. The non-transitory computer-readable medium of claim 14, where the initial value of the time interval is determined by an equation provided for a non-discrete τ-leaping algorithm.

17. The non-transitory computer-readable medium of claim 16, where a state of the model at time (t+τ) is a function of a state of the model at time t.

18. The non-transitory computer-readable medium of claim 13, where the instructions further include:
one or more instructions to determine the leap condition based on a user-defined tolerance of a relative change in a state of the model.

19. The non-transitory computer-readable medium of claim 13, where the lower limit satisfies the leap condition and the upper limit does not satisfy the leap condition.

20. The non-transitory computer-readable medium of claim 13, where the initial value of the time interval is increased or decreased using a predetermined ratio.

21. The non-transitory computer-readable medium of claim 13, where the instructions further include:
one or more instructions to determine a point between the lower limit and the upper limit; and
one or more instructions to determine whether the point satisfies the leap condition.

22. The non-transitory computer-readable medium of claim 21, where the instructions further include:
one or more instructions to update, a first time, the lower limit with the point when the point satisfies the leap condition; or
one or more instructions to update, a first time, the upper limit with the point when the point does not satisfy the leap condition.

23. The non-transitory computer-readable medium of claim 22, where the instructions further include:
one or more instructions to update the lower limit a second time;
one or more instructions to update the upper limit a second time; and
one or more instructions to set, based on updating the lower limit the second time and updating the upper limit the second time, a size of the time interval to the lower limit.

24. The non-transitory computer-readable medium of claim 13, where a plurality of discrete events, associated with the model, are associated with at least two different time scales.

25. A device comprising:
a memory to store instructions; and
one or more processors to execute the instructions to:
  determine an initial value of a time interval for execution of a model,
    the model being associated with a chemical system or a biological system;
  adjust the initial value of the time interval using a bracketing algorithm, the one or more processors, when adjusting the initial value, being to:
    provide an upper limit for the time interval and a lower limit for the time interval; and
    determine, a first time, if a leap condition is satisfied for the model over the time interval, the one or more processors, when determining if the leap condition is satisfied, being to:
      set the lower limit for the time interval as the initial value and increase the initial value when the leap condition is satisfied, and
      set the upper limit for the time interval as the initial value and decrease the initial value when the leap condition is not satisfied,
  compare a distance between the lower limit and the upper limit to a predetermined distance,
    the lower limit being selected as a final time interval when the distance between the lower limit and the upper limit is less than the predetermined distance, and
    the determination if the leap condition is satisfied being performed a second time when the distance between the lower limit and the upper limit is greater than the predetermined distance;
  simulate the chemical system or the biological system using the model and using time steps corresponding to the final time interval to generate a simulation result; and
  output the simulation result for analysis.

26. The device of claim 25, where a leaping algorithm, used to determine the initial value, comprises a tau($\tau$)-leaping algorithm.

27. The device of claim 26, where a state of the model at time (t+$\tau$) is a function of a state of the model at time t and the state of the model at time (t+$\tau$).

28. The device of claim 27, where the initial value of the time interval is determined by an equation provided for a non-discrete $\tau$-leaping algorithm.

29. The device of claim 25, where the one or more processors are further to:
  determine the leap condition based on a user-defined tolerance of a relative change in a state of the model.

30. The device of claim 25, where the one or more processors are multiple central processing units (CPUs).

31. The device of claim 25, where the one or more processors comprise a multiple core processor.

32. The device of claim 25, where the one or more processors support one or more virtual machines.

33. The device of claim 25, where the one or more processors comprise a field programmable gate array (FPGA) or an application specific integrated circuit (ASIC).

34. The device of claim 25, where a plurality of discrete events, associated with the model, are associated with at least two different time scales.

* * * * *